United States Patent [19]

Fleet

[11] Patent Number: 5,023,340
[45] Date of Patent: Jun. 11, 1991

[54] PYRROLIZIOINES AND SYNTHESIS THEREOF

[75] Inventor: George W. J. Fleet, Oxford, United Kingdom

[73] Assignee: Monsanto Company, St. Louis, Mo.

[21] Appl. No.: 424,628

[22] Filed: Oct. 20, 1989

[51] Int. Cl.$^5$ ............................................ C07D 487/04
[52] U.S. Cl. .................................. 548/453; 548/428; 548/430
[58] Field of Search ........................................ 548/453

[56] References Cited

PUBLICATIONS

Fleet et al., J. Chem. Soc. Chem. Commun., 1240–1241 (1984).
Cenci di Bello et al., Biochyem. J. 259, 855 14 861 (1989).
Al Daher et al., Biochem. J. 258, 613–615 (1989).
Bashyal et al., Tetrahedron 43, 3083–3093 (1987).
Dener et al., J. Org. Chem. 53, 6022 (1988).
Bennett et al., J. Am. Chem. Soc. 111, 2580 (1989).
Fleet et al., Tetrahedron 44, 2649–2655 (1988).
Setoi et al., J. Org. Chem. 50, 3948 (1985).

Primary Examiner—David B. Springer
Attorney, Agent, or Firm—Scott J. Meyer; James W. Williams, Jr.

[57] ABSTRACT

Swainsonine and analogs, namely, 1,4-dideoxy-1,4-imino-D-mannitol and the novel ring contacted swainsonines, (1S,2R,7R,7aR)-1,2-trihydroxypyrrolizidine and (1S,2R,7S,7aR)-1,2,7-trihydroxypyrrolizidine, are synthesized from the divergent intermediate, 4,5-anhydro-1-azido-1-deoxy-2,3-O-isopropylidene-D-talitol. These novel compounds are glycosidase inhibitors.

4 Claims, No Drawings

PYRROLIZIOINES AND SYNTHESIS THEREOF

BACKGROUND OF THE INVENTION

This invention relates to the syntheses of swainsonine and analogs thereof.

Swainsonine (1), a potent and specific inhibitor of lysosomal and some of the processing forms of α-mannosidase [Cenci di Bello et al., *Biochem. J.* 215, 693 (1983); Tulsiani et al., *J. Biol. Chem.* 257, 7936 (1982)], may have therapeutic value as an antimetastic [Humpheries et al., *Cancer Res.* 48, 1410 (1988)], and tumor-proliferative [Dennis, *Cancer Res.* 46, 5131 (1986)], or immunoregulatory agent [Kino et al., *J. Antibiot.* 38, 936 (1985)]. Studies on the inhibition of human α-mannosidase by swainsonine analogs such as 1,4-dideoxy-1,4-imino-D-mannitol (DIM) (2) [Fleet et al., *J. Chem. Soc. Chem. Commun.* 1984, 1240; Palamarczyk et al., *Arch. Biochem. Biophys.* 243, 35 (1985); Daniel et al., *Glycoconjugate J.* 6, 229 (1989)] have recently been reported [Cenci di Bello et al., *Biochem. J.* 259, 855 (1989)]. N-Alkylation of open chain swainsonine analogues effectively removes all ability to inhibit α-mannosidase [Al Daher et al., *Biochem. J.* 258, 613 (1989)]; it is therefore of interest to determine the effect of variation of the size of the six-membered ring of swainsonine on the inhibition of mannosidases. There has been much interest in the synthesis of swainsonine [Bashyal et al., *Tetrahedron* 43, 3083–3093 (1987); Dener et al., *J. Org. Chem.* 53, 6022 (1988), and references cited therein], and, in particular, in procedures that could produce significant quantities of material [Bennett et al., *J. Am. Chem. Soc.* 111, 2580 (1989)].

BRIEF DESCRIPTION OF THE INVENTION

In accordance with the present invention, a novel method for the syntheses of swainsonine and analogs thereof from mannose is provided. By this method 4,5-Anhydro-1-azido-1-deoxy-2,3-O-isopropylidene-D-talitol (6) is used as a divergent intermediate for the efficient and practical syntheses of 1,4-dideoxy-1,4-imino-D-mannitol (2), swainsonine (1) and of the ring contracted swainsonines, (1S, 2R, 7R, 7aR)-1,2,7-trihydroxypyrrolizidine (3) and (1S, 2R, 7S, 7aR)-1,2,7-trihydroxypyrrolizidine (4). The latter compound (4) is structurally related to the pyrrolizidine alkaloid 1,7a-diepialexine (5), recently isolated from *Castanospermum australe* and demonstrated to be a powerful amyloglucosidase inhibitor [Nash et al., *Phytochemistry*, In Press 1989].

The ring contracted swainsonines (1S, 2R, 7R, 7aR)-1,2,7-trihydroxypyrrolizidine (3) and the 7S-epimer (4), are novel compounds and inhibitors of glycosidases but have weaker such activity than swainsonine.

Syntheses of 1,4-dideoxy-1,4-imino-D-mannitol (2), swainsonine (1) and the ring contracted swainsonines (3) and (4) from the divergent intermediate, 4,5-anhydro-1-azido-1-deoxy-2,3-O-isopropylidene-D-talitol (6), is preferably carried out by the stepwise method as follows in which compound numbers in parentheses correspond to compounds shown by chemical structure herein:

Synthesis of 1,4-Dideoxy-1,4-Imino-D-Mannitol (a) 4,5-Anhydro-1-azido-1-deoxy-2,3-O-isopropylidene-D-talitol (6) is catalytically hydrogenated, e.g. in the presence of palladium on carbon, to provide ring closure and give the protected pyrrolidine (13), and (b) The isopropylidene protecting group in the protected pyrrolidine (13) is removed by acid hydrolysis to give 1,4-dideoxy-1,4-imino-D-mannitol.

Syntheses of Swainsonine (a) 4,5-Anhydro-1-azido-1-deoxy-2,3-O-isopropylidene-D-talitol (6) is esterified at the primary hydroxyl with triflic anhydride to give the triflate (9), (b) The triflate (9) is reacted with lithium tert-butyl acetate to give the chain extended azidoester (14), (c) The azidoester (14) is catalytically hydrogenated, e.g. with palladium on carbon, to give the aminoester (16), (d) The aminoester (16) is heated with sodium methoxide to provide ring closure and give the δ-lactam (17), (e) The δ-lactam (17) is reduced with borane:-dimethyl sulfide to give the aminoborane adduct or complex (18) and (f) The isopropylidene protecting group in aminoborane adduct (18) and the borane group are removed by acid hydrolysis to give the desired swainsonine (1).

Synthesis of (1S, 2R, 7R, 7aR)-1,2,7-Trihydroxypyrrolizidine (3)

(a) Triflate (9) is reacted with lithium cyanide to form the azidocyanoepoxide or nitrile (15), (b) The azidocyanoepoxide (15) is catalytically hydrogenated, e.g. with palladium on carbon, to give the amine (19), (c) Protection of the nitrogen on amine (19) is carried out by reaction with benzyl chloroformate to give the benzyloxycarbonyl derivative (20), (d) The benzyloxycarbonyl derivative (20) is partially hydrolyzed at the nitrile group by hydrogen peroxide to give the amide (21), (e) The amide (21) is silylated to give the protected amine (22), (f) The benzyloxycarbonyl protecting group is removed by acid hydrolysis of the protected amine (22) to give the aminoamide (23), (g) The aminoamide (23) is treated with sodium hydrygen carbonate to give the silyl alcohol or lactam (24), (h) the lactam (24) is treated with borane:dimethyl sulfide complex to afford the amine borane adduct (26), and (i) The isopropylidene and silyl protecting groups and the borane group in the amine borane adduct (26) are removed by acid hydrolysis to give the desired ring contracted swainsonine, (1S, 2R, 7R, 7aR)-1,2,7-trihydroxypyrrolizidine (3).

Synthesis of (1S, 2R, 7S, 7aR)-1,2,7-Trihydroxy-pyrrolizidine (4)

(a) The silyl alcohol or lactam (24) is reacted with fluoride ion to remove the silyl protecting group and give alcohol (25), (b) The alcohol (25) is oxidized, e.g. with pyridinium chlorochromate, to give the corresponding ketone (28), (c) The ketone (28) is reduced, e.g. with sodium borohydride, to give the inverted alcohol or lactam (29), (d) The lactam (29) is reduced with borane:dimethyl sulfide complex to afford the borane adduct (27), and (e) The isopropylidene protecting group and the borane group in borane adduct (27) are removed by acid hydrolysis to give the desired ring contracted swainsonine, (1S, 2R, 7S, 7aR)-1,2,7-trihydroxypyrrolizidine (4).

Other such suitable reactants for use in the foregoing syntheses of 1,4-dideoxy-1,4-imino-D-mannitol (2), swainsonine (1) and the ring contracted swainsonines (3) and (4) will be apparent to the person skilled in the art after reading the present disclosure. These reactants are generally used in proportions such as to satisfy the stoichiometry of the above reaction steps. Illustrative of suitable reactants are the use of a noble metal catalyst such as platinium or palladium on carbon for the catalytic hydrogenation; use of tert-butyldimethylsilyl chloride or tert-butyldiphenylsilyl chloride to introduce the silyl protecting groups; use of hydroxyl protecting groups such a isopropylidene or cyclohexylidene; use of tetrabutylammonium fluoride to remove the silyl protecting groups; use of trifluoroacetic acid for the hydrolytic removal of protecting groups; and use of organic solvents such as dioxane, DMF, THF, DMSO, N-methylpyrrolidine, acetonitrile and the like as solvent media for the reaction steps.

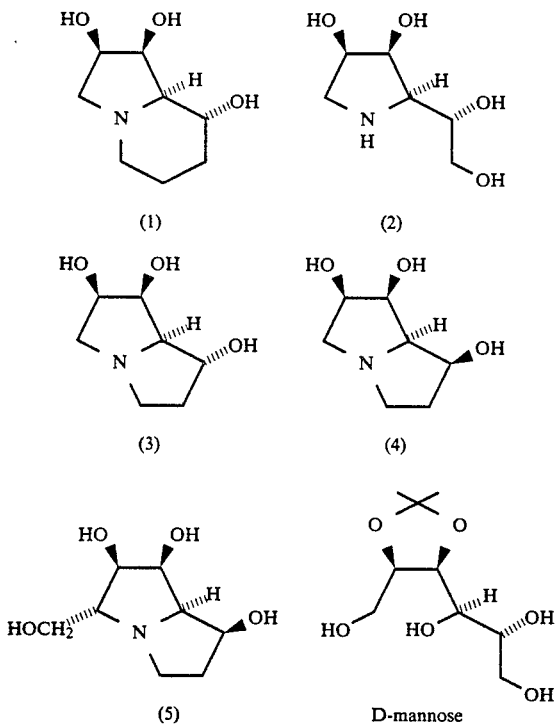

DETAILED DESCRIPTION OF THE INVENTION

The invention is conveniently illustrated by the following description of the preferred embodiments in which 4,5-Anhydro-1-azido-1-deoxy-2,3-O-isopropylidene-D-talitol (6) is derived from mannose by introduction of an azido group at C-1 and by a single inversion at C-4 and then used as a readily available divergent intermediate for the synthesis of the desired swainsonine and analogs thereof. The synthesis of all these synthetic compounds requires the introduction of nitrogen at C-4 of mannose with overall retention, that is double inversion, of configuration. The dimesylate (10), readily available on a large scale from mannose in an overall yield of 80% [Fleet et al., Tetrahedron 44, 2649 (1988)], undergoes selective displacement of the primary mesylate by sodium azide in N,N-dimethylformamide:water to give the azidomesylate (11), [62% yield; 87% based on recovered (10)] which, on partial hydrolysis in aqueous methanol with camphor sulphonic acid, affords the diol (12), m.p. 82°–84° C., $[\alpha]_D^{20}$ +90.8° (c, 0.51 in CHCl$_3$) in 56% yield [81% based on unrecovered dimesylate (10)]. Treatment of (12) with saturated methanolic barium methoxide [Kusman and Kiss, Carbohydr. Res. 153, 45 (1986) and references cited therein] gave the azido epoxide (6) in 95% yield. The azidoepoxide (6) is moderately unstable at room temperature and the material was used immediately; (6) was fully characterized as the stable tert-butyldimethylsilyl (7) and tert-butyldiphenylsilyl (8) ethers.

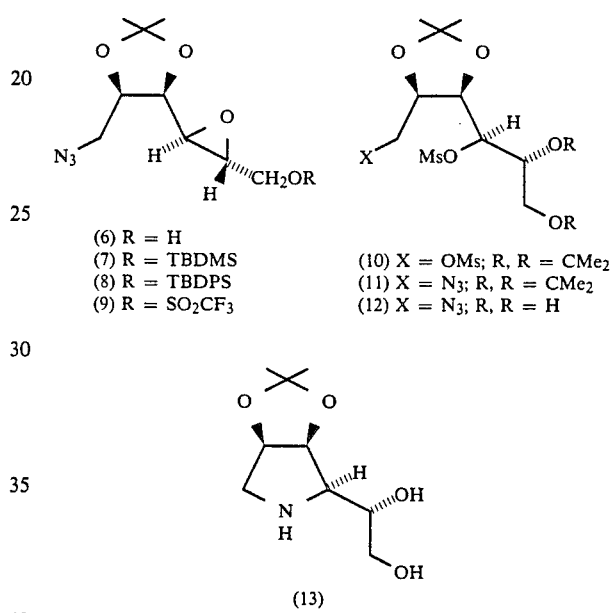

Hydrogenation of the azide (6) in 1,4-dioxane:water in the presence of palladium on carbon gave the protected pyrrolidine (13), m.p. 86°–88° C. [lit. 86°–88° C.] in 90% yield [31% overall yield from mannose; 45% from diacetone mannose]; removal of the isopropylidene protecting group from (13) by aqueous trifluoroacetic acid, followed by conversion to the hydrochloride salt, afforded DIM (2) as the hydrochloride, m.p. 149°–151° C. [lit. m.p. 148°–149° C.], identical to authentic material [Bashyal et al., Tetrahedron Lett. 28, 4189 (1987)].

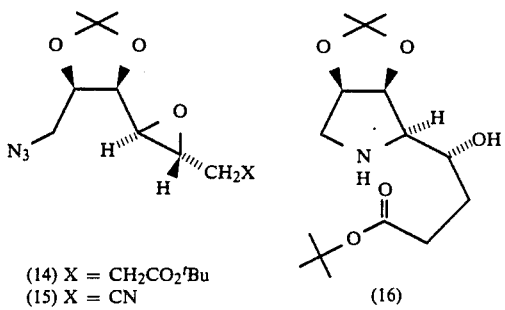

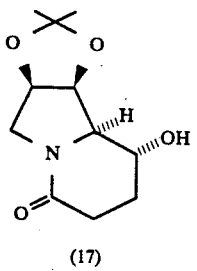
(17)

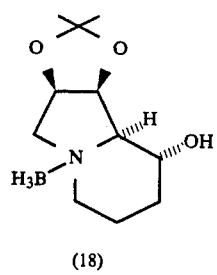
(18)

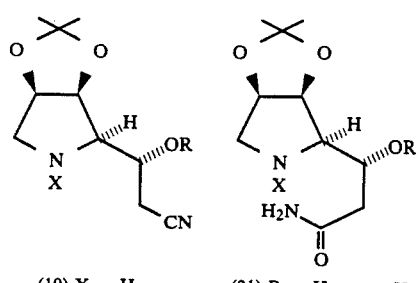

(19) X = H
(20) X = Z

(21) R = H;  X = Z
(22) R = TBDMS; X = Z
(23) R = TBDMS; X = H

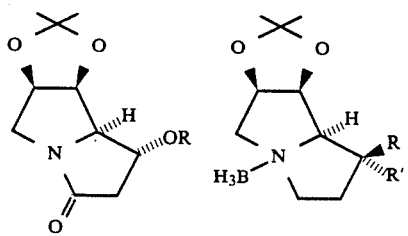

(24) R = TBDMS
(25) R = H

(26) R = H;  R' = OTBDMS
(27) R = OH; R' = H

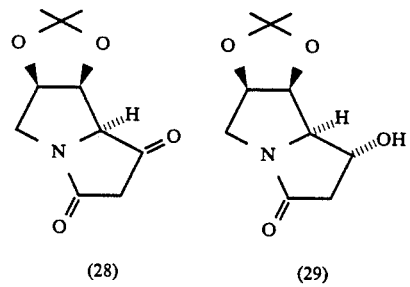

(28)          (29)

The two carbon extension for the synthesis of swainsonine was achieved by initial esterification of the primary alcohol by trifluoromethanesulphonic anhydride to give the triflate (9) which was reacted with lithium tert-butyl acetate in tetrahydrofuran to give the chain extended ester (14), an oil, $[\alpha]_D^{20}$ +63.5° (c, 0.98 in $CHCl_3$) in 60% overall yield from the azidomesylate (12). Hydrogenation of the azidoester (14) in ethanol with palladium on carbon as the catalyst gave the aminoester (16) (80% yield) which on heating with sodium methoxide in methanol gave the δ-lactam (17), m.p. 126°-128° C. [lit.*m.p. 125°-127° C.], in 92% yield. [*Setoi et al., *J. Org. Chem.* 30, 3948 (1985)]. Reduction of the lactam (17) by borane:dimethyl sulphide gave the non-polar borane adduct (18) [70% yield] which was easily purified by flash chromatography; treatment of (18) with aqueous trifluoroacetic acid gave, after purification by ion exchange chromatography, swainsonine (1), m.p. 126°-128° C. [lit. m.p. 125°-127° C.], in 86% yield [12% from mannose; 18% from diacetone mannose], identical to an authentic sample. Satisfactory spectral data were obtained for all new compounds disclosed herein; correct CHN microanalytical data was obtained for compounds (3), (4), (7), (8), (12), (13), (14), (17), (19), (20), (21), (22), (24), (25), and (29). For (6), $\delta_C$ ($CDCl_3$): 110.0 (s), 76.54 and 76.44 (2d, C-2 and C-3), 60.8 (t, C-6), 56.7 and 52.3 (2d, C-4 and C-5), 50.3 (t, C-1), 27.2 and 24.7 (2q).

The synthesis of the ring contracted swainsonines requires a one carbon extension of the azidotriflate (9). Treatment of (9) with lithium cyanide resulted in the formation of the nitrile (15) [77% yield from (12)]; the use of lithium cyanide in this displacement is critical [Harusawa et al., *Tetrahedron Lett.* 28, 4189 (1987)]. Hydrogenation of (15) in ethanol with a catalyst of palladium on carbon gave (19), m.p. 92°-92° C., $[\alpha]_D^{20}$ −77.2° (c, 0.32 in $CHCl_3$) in 73% yield. Protection of the nitrogen as the benzyloxycarbonyl (Z) derivative (20), followed by partial hydrolysis of the nitrile by hydrogen peroxide in methanol in the presence of hexene gave the amide (21) which was silylated to (22) and the Z-protecting group removed to give (23), m.p. 143°-144° C., $[\alpha]_D^{20}$ −55.0° (c, 0.26 in $CHCl_3$) [75% yield from (19)]. Treatment of the aminoamide (23) with a suspension of sodium hydrogen carbonate in carbon tetrachloride gave the lactam (24), m.p. 106°-109° C. (92% yield) which on treatment with borane:dimethyl sulphide afforded the amine borane adduct (26) (70% yield) which with aqueous trifluoroacetic acid and purification by ion exchange chromatography gave the ring contracted swainsonine (3), m.p. 150°-153° C., $[\alpha]_D^{20}$ −29.3° (c, 0.15 in MeOH) [68% yield].

The epimeric trihydroxypyrrolizidine (4) was obtained by inversion of the free hydroxy group in (25), m.p. 148°-149° C., $[\alpha]_D^{20}$ 0° (c, 0.30 in $CHCl_3$), prepared by the removal of the silyl protecting group in (24) by fluoride (100% yield). Oxidation of (25) by pyridinium chlorochromate gave the ketone (28) which, on treatment with sodium borohydride in ethanol, cleanly gave the inverted alcohol (29), m.p. 132°-134° C., $[\alpha]_D^{20}$ −19.3° (c, 0.46 in $CHCl_3$), [94% yield from (25)]. Reduction of lactam (29) with borane:dimethyl sulphide afforded the borane adduct (27) (72% yield) which with aqueous trifluoroacetic acid and purification by ion exchange chromatography gave (4). m.p. 125°-127° C., $[\alpha]_D^{20}$ −6.9° (c, 0.13 in MeOH), in 70% yield. For (3), $\delta_C$ ($D_2O$): 73.74 and 73.14 (2d, C-1 and C-2), 70.9 (d, C-7), 70.6 (d, 7a), 56.0 (d, C-3), 53.5 (t, C-5), 34.8 (t, C-6). For (4), $\delta_C$ ($D_2O$): 73.14 (d, C-1 and C-2), 72.8 (d, C-7), 68.0 (d, C-7a), 57.3 (d, C-3), 53.5 (t, C-5), 35.6 (t, C-6).

The effects of the ring contracted swainsonines (3) and (4) on the inhibition of 14 human liver glycosidases was studied by the assay methods described in Palamarczyk et al., *Arch. Biochem. Biophys.* 243, 35 (1985); Daniel et al., *Glycoconjugate J.* 6, 229 (1989) and Cenci di Bello et al., *Biochem. J.* 259, 855 (1989). The pyrrolizidine analog of swainsonine (3) is a weak inhibitor of lysosomal α-mannosidase ($I_{50}$ 1.5×10$^{-3}$M) compared with swainsonine (1) (Ki 7×10$^{-8}$M); (3) is also less effective in inhibiting the Golgi II and neutral processing mannosidases. At a concentration of 1 mM (3) also inhibited the β-galactosidase by 69%, the broad specificity β-galactosidase/β-glucosidase moderately (25%) and the α-fucosidase by 33%. The inhibition of Jack bean α-mannosidase by (3) is also very weak ($K_i$ $1.7 \times 10^{-3}$M) in comparison to the inhibition by swainsonine [*J. Chem. Soc. Chem. Commun.* 1984, pp. 1240–1241]; also no significant inhibition by (3) was observed of the following glycosidases: snail β-mannosidase, yeast α-glucosidase, almond β-glucosidase, *Aspergillus niger* and green coffee bean α-galactosidases, bovine β-galactosidase, bovine kidney α-fucosidase, or bovine β-hexosaminidase.

The epimeric pyrrolizidine (4), which corresponds to 8-epi-swainsonine, does not inhibit human liver α-mannosidases but is a weak inhibitor of the broad specificity β-galactosidase/β-glucosidase (40%); in this (4) resembles the specificity of glycosidases shown by 8-epi-swainsonine [Cenci di Bello et al., *Biochem. J.* 259, 855 (1989)].

The following examples will further illustrate the invention in greater detail although it will be appreciated that the invention is not limited to these specific examples. The starting dimesylate (10) was synthesized as described by Fleet et al., *Tetrahedron* 44, 2649–2655 (1988), by converting diacetone mannose into the corresponding diol, 1,2:4,5-di-O-isopropylidene-D-mannitol, and then esterifying the diol with methanesulfonyl chloride to give dimesylate (10).

Examples 1 to 3 illustrate the syntheses of the divergent intermediate, 4,5-anhydro-1-azido-1-deoxy-2,3-O-isopropylidene-D-talitol (6), from the dimesylate (10). Examples 4 and 5 illustrate the preparation of the tert-butyldimethylsilyl (7) and tert-butyldiphenylsilyl (8) ethers of (6). Examples 6 and 7 illustrate the synthesis of 1,4-dideoxy-1,4-imino-D-mannitol from the divergent intermediate (6). Examples 8 to 13 illustrate the synthesis of swainsonine (1) from the divergent intermediate (6). Examples 14 to 22 illustrate the synthesis of ring contracted swainsonine (3) starting from the epoxytriflate (9) made in the swainsonine synthesis, while Examples 23 to 27 illustrate the synthesis of ring contracted swainsonine (4), starting from the silyl alcohol (24) made in the synthesis of the ring contracted swainsonine (3).

METHODS

Melting points were recorded on a Kofler hot block and are uncorrected. Infrared spectra were recorded on a Perkin-Elmer 297 spectrophotometer or a Perkin-Elmer 1750 FT spectrophotomether as a thin film unless otherwise stated. $^1$H NMR spectra were run at 300 MHZ on a Bruker WH 300 spectrometer (500 MHz on a Bruker AM 500 spectrometer). $^{13}$C NMR spectra were recorded on a Varian Gemini 200 (50 MHz) or a Bruker 250 (62.9 MHz) spectrometer. Multiplicities were assigned using DEPT sequence on the Gemini and by off resonance decoupling on the Bruker. Spectra were run in deuteriochloroform unless otherwise stated, using residual protonated solvent as an internal standard. $^{13}$C D$_2$O spectra use 1,4-dioxane or methanol as the internal standard. Mass spectra were recorded on VG Micromass 30F, ZAB IF or Masslab 20–250 spectrometers. Desorption chemical ionization (DCI, NH$_3$) and chemical ionization (CI, NH$_3$) techniques were used. Optical rotations were measured on a Perkin-Elmer 241 polarimeter with a path length of 1 dm. Concentrations were given in g/100 ml. Microanalyses were performed by the microanalysis service of the Dyson-Perrins Laboratory, Oxford, U.K. Thin layer chromatography (t.l.c.) was carried out on aluminum sheets pre-coated with 60F$_{254}$ silica. Plates were developed using either 5% v/v concentrated sulphuric acid in methanol, 0.2% w/v cerium (IV) sulphate and 5% ammonium molybdate in 2M sulphuric acid or 0.5% ninhydrin in methanol. Flash chromatography was carried out using Merck Keiselgel 60 (0.04–0.063 mm). Solvents were dried according to the following procedures: Dichloromethane was refluxed over and distilled from calcium hydride. N,N-dimethylformamide was distilled under reduced pressure from calcium hydride. Methanol was distilled from magnesium methoxide. Pyridine was distilled from and stored over potassium hydroxide. Tetrahydrofuran was distilled from a purple solution of sodium benzophenone ketyl immediately before use. Hexane was distilled at 68° C. before use to remove involatile fractions. Hydrogenations were executed at atmospheric pressure of hydrogen gas maintained by inflated balloon.

EXAMPLE 1

1-Azido-1-deoxy-2,3:5,6-di-O-isopropylidene-4-O-methanesulphonyl-D-mannitol (11)

To the dimesylate (10) (13 g, 31 mmol) in dimethylformamide:water (9:1, 130 ml) was added all at once sodium azide (6 g, 93 mmol). The reaction mixture was then stirred at 90° C. for 18 hours. T.l.c. (50%, ethyl acetate/hexane) then showed starting material ($R_f$0.35) and product ($R_f$0.55). The solvent was then removed in vacuo to give a pale brown residue which was taken up in ether (150 ml) and washed with water (100 ml). The water was then back extracted with ether (50 ml). The combined ethereal extracts were then washed with brine (4×50 ml) before being dried (sodium sulphate). Removal of the solvent followed by flash chromatography (0–80%, ethyl acetate/hexane) gave 1-azido-1-deoxy-2,3:5,6-di-O-isopropylidene-4-O-methanesulphonyl-D-mannitol (11), (7 g, 62%) as a colourless oil. $v_{max}$: 2104 cm$^{-1}$. $^1$H NMR ∂: 4.75 (1H, t, H-4), 4.4–4.0 (5H, m, H-2, H-3, H-5, H-6, H-6'), 3.5 (2H, m, H-1, H-1'), 3.17 (3H, s, SCH$_3$), 1.57, 1.44, 1.40, 1.36 (12H, 4s, CH$_3$). $^{13}$C NMR ∂: 110.5, 109.4 (2s, C(CH$_3$)$_2$), 78.8, 76.6, 76.2, 74.8 (4d, C-2, C-3, C-34, C-5), 67.0 (t, C-6), 50.9 (t, C-1), 39.0 (q, SCH$_3$), 27.4, 25.8, 25.5, 24.8 (4q, CH$_3$). m/z (DCI, NH$_3$): 383 (M+NH$_4$+, 15%), 338 (M+H—N$_2$+, 100%). Starting dimesylate was also recovered (3.8 g, 30%).

EXAMPLE 2

1-Azido-1-deoxy-2,3-O-isopropylidene-4-O-methanesulphonyl-D-mannitol (12)

To the azidomesylate (11) (10 g, 27.4 mmol) was added methanol:water (10:1, 33 ml), followed by camphorsulphonic acid (30 mg). The solution was then stirred for 2 hours at 50° C. by which time t.l.c. (50%, ethyl acetate/hexane) showed the reaction to be about 30% complete. The acid was then neutralised with 0.880 ammonia solution before the solvent was removed in vacuo. Preadsorption onto silica gel and purification by flash chromatography (30% ethyl acetate/hexane followed by neat ethyl acetate) gave starting material and product. The recovered starting material was then twice recycled by the same procedure to give 1-azido-1-deoxy-2,3-O-isopropylidene-4-O-methanesulphonyl-D-mannitol (12), (5 g, 56%) m.p. 82°–84° C. (ethyl acetate/hexane). $[\alpha]_D^{20}$ +90.8° (c, 0.51 in CHCl$_3$). $\nu_{max}$: 3400, 2104 cm$^{-1}$. $^1$H NMR ∂: 4.80 (1H, t, H-4), 4.43 (2H, m, H-2, H-3), 3.90-3.72 (3H, m, H-5, H-6, H-6'), 3.54 (2H, d, H-1, H-1'), 3.18 (3H, SCH$_3$), 2.90 (1H, d, OH), 2.30 (1H, t, OH), 1.55, 1.41 (6H, 2s, CH$_3$). $^{13}$C NMR ∂: 109.0 (s, C(CH$_3$)$_2$), 78.7, 76.5, 71.9 (3d, C-2, C-3, C-4, C-5), 62.1 (t, C-6), 51.1 (t, C-1), 38.9 (q, SCH$_3$), 27.4, 25.4 (2q, CH$_3$). m/z (DCI, NH$_3$): 343 (M+NH$_4^+$, 50%), 298 (M+H—N$_2^+$, 100%), 202 (M+H—N$_2$—HOSO$_2$Me$^+$, 40%), 142 ((202—HOCH$_2$CHOH)$^+$, 40%). (Found C, 36.66; H, 5.83; N, 12.63%. C$_{10}$H$_{19}$N$_3$O$_7$S requires C, 36.92; H, 5.85; N, 12.92%) and starting material (3.1 g, 31%).

EXAMPLE 3

4,5-Anhydro-1-azido-1-deoxy-2,3-O-isopropylidene-D-talitol (6)

To the diol (12) (2.88 g, 8.86 mmol) in freshly distilled, dry methanol (20 ml) was added a saturated barium methoxide solution (4 ml). The reaction was then stirred for 30 minutes at room temperature by which time no starting material (R$_f$0.2) remained and only one product (R$_f$0.25) was visible by t.l.c. (50%, ethyl acetate/hexane). Carbon dioxide (solid) was then added followed by silica gel. Removal of the solvent in vacuo and flash chromatography (0-70%, ethyl acetate/hexane) then gave 4,5-anhydro-1-azido-1-deoxy-2,3-O-isopropylidene-D-talitol (6), as a colourless oil (1.9 g, 95%). $[\alpha]_D^{20}$ +77.3° (c, 0.51 in CHCl$_3$). $\nu_{max}$: 3500, 2104 cm$^{-1}$. $^1$H NMR ∂: 4.38 (1H, m, H-2), 4.08-3.62 (3H, m, H-3, H-6, H-6'), 3.54 (2H, m, H-1, H-1'), 3.09 (2H, m, H-4, H-5), 2.30 (1H, s, OH), 1.50, 1.35 (6H, 2s, CH$_3$). $^{13}$C NMR ∂: 110.0 (s, C(CH$_3$)$_2$), 76.5, 76.4, (2d, C-2, C-3), 60.8 (t, C-6), 57.6 (d, C-5), 52.3 (2d, C-4, C-5), 50.3 (t, C-1), 27.2, 24.7 (2q, CH$_3$). m/z (DCI, NH$_3$): 247 (M+NH$_4^+$, 5%), 230 (M+H$^+$, 4%), 202 (M+H—N$_2^+$, 70%), 184 (M+H—N$_2$—H$_2$O$^+$, 50%), 142 (100%).

EXAMPLE 4

4,5-Anhydro-1-azido-6-O-tert-butyldimethylsilyl-1-deoxy-2,3-O-isopropylidene-D-talitol (7)

To the epoxy alcohol (6) (0.4 g, 1.75 mmol) in freshly distilled, dry dimethylformamide (10 ml) was added recrystallised imidazole (340 mg, 5.24 mmol) and tert-butyldimethylsilyl chloride (400 mg, 2.62 mmol). The reaction mixture was then stirred at room temperature for 12 hours. The solvent was then removed in vacuo and the residue taken up in diethyl ether (40 ml) before being washed with water (10 ml), then brine (3×15 ml), dried (sodium sulphate) and purified by flash chromatography (0-20%, ethyl acetate/hexane) to give 4,5-anhydro-1-azido-6-O-tert-butyldimethylsilyl-1-deoxy-2,3-O-isopropylidene-D-talitol (7), as a colourless oil. (0.54 g, 90%). +51.8° (c, 1.2 in CHCl$_3$). $\nu_{max}$: 3500, 3019, 2107 cm$^{-1}$. $^1$H NMR ∂: 4.37 (1H, m, H-2), 3.90 (1H, dd, H-6), 3.86 (1H, t, H-3), 3.66 (1H, dd, H-6'), 3.54 (2H, m, H-1, H-1'), 3.03 (1H, quin., H-5), 2.95 (1H, dd, H-4), 1.49, 1.34 (6H, 2s, CH$_3$), 0.87 (9H, s, C(CH$_3$)$_3$), 0.04 (6H, s, SiCH$_3$). $^{13}$C NMR ∂: 109.9 (s, C(CH$_3$)$_2$), 76.7, 76.5 (2d, C-2, C-3), 62.2 (t, C-6), 57.8 (d, C-5), 52.1 (d, C-4), 50.3 (t, C-1), 27.3 (q, CH$_3$), 25.6 (q, C(CH$_3$)$_3$), 24.8 (q, CH$_3$), 18.0 (s, C(CH$_3$)$_3$), −5.6 (q, SiCH$_3$). m/z (DCI, NH$_3$): 361 (M+NH$_4^+$, 3%), 344 (M+H$^+$, 1%), 316 (M+H—N$_2^+$, 100%), 142 (100%). (Found C, 52.36; H, 8.79; N, 12.53%. C$_{15}$H$_{29}$N$_3$O$_4$Si requires C, 52.47 H, 8.45; N, 12.24%).

EXAMPLE 5

4,5-Anhydro-1-azido-6-O-tert-butyldiphenylsilyl-1-deoxy-2,3-O-isopropylidene-D-talitol (8)

To the epoxy alcohol (6) (0.6 g, 2.62 mmol) in freshly distilled, dry N,N-dimethylformamide (10 ml) was added recrystallised imidazole (0.5 g, 7.86 mmol) and tert-butyldiphenylsilyl chloride (1 ml, 3.93 mmol). The reaction mixture was then stirred at room temperature for 12 hours by which time no starting material remained (R$_f$0.3) and one product was formed (R$_f$0.9) by t.l.c. (50%, ethyl acetate/hexane). Removal of the solvent in vacuo followed by flash chromatography (0-20%, ethyl acetate/hexane) then gave 4,5-anhydro-1-azido-6-O-tert-butyldiphenylsilyl-1-deoxy-2,3-O-isopropylidene-D-talitol (8), as a colourless oil (1.5 g, >100%) contaminated with tert-butyldiphenylsilyl alcohol. $[\alpha]_D^{20}$ +34.1° (c, 0.46 in CHCl$_3$). $\nu_{max}$: 3400, 3000, 2106 cm$^{-1}$. $^1$H NMR ∂: 7.67 (4H, m, ArH), 7.42 (6H, m, ArH), 4.40 (1H, m, H-2), 3.94 (1H, dd, H-6), 3.85 (1H, t, H-3), 3.74 (1H, dd, H-6'), 3.56 (2H, m, H-1, H-1'), 3.12 (1H, quin., H-5), 3.05 (1H, dd, H-4), 1.53, 1.38 (6H, 2s, CH$_3$), 1.06 (9H, s, C(CH$_3$)$_3$). $^{13}$C NMR ∂: 135.8, 133.0, 129.9, 127.9 (Ar), 110.0 (s, C(CH$_3$)$_2$), 76.8, 76.6 (2d, C-2, C-3), 62.8 (t, C-6), 57.7 (d, C-5), 52.2 (d, C-4), 27.4 (q, CH$_3$), 26.6 (q, C(CH$_3$)$_3$), 24.9 (q, CH$_3$). m/z (DCI, NH$_3$): 485 (M+NH$_4^+$, 10%), 440 (M+H—N$_2^+$, 75%), 142 (100%). (Found C, 64.29; H, 7.37; N, 8.61%. C$_{25}$H$_{33}$N$_3$O$_4$Si requires C, 64.23; H, 7.07; N, 8.99%).

EXAMPLE 6

1,4-dideoxy-1,4-imino-2,3-O-isopropylidene-D-mannitol (13)

The epoxide (6) (1.8 g, 8.4 mmol) was stirred in 1,4-dioxane:water (1:1, 20 ml) under hydrogen in the presence of 10% palladium on carbon (100 mg) for 18 hours by which time no starting material (R$_f$0.25) remained by t.l.c. (50%, ethyl acetate/hexane). Filtration and evaporation then gave the crude aminodiol which was purified by ion exchange chromatography to give 1,4-dideoxy-1,4-imino-2,3-O-isopropylidene-D-mannitol (13), as an oil which crystallised on standing (1.55 g, 90%). This was shown to be identical to authentic material. m.p. 86°-88° C. (lit. 86°-88° C.).

EXAMPLE 7

1,4-Dideoxy-1,4-imino-D-mannitol (2)

The diol (13) (500 mg, 2.46 mmol) was dissolved in trifluoroacetic acid:water (9:1, 0.5 ml) and stirred for 48 hours at room temperature. Removal of the solvent in vacuo and purification by ion exchange chromatography then gave 1,4-dideoxy-1,4-imino-D-mannitol (2), (33 mg, 73%) as a hygroscopic white solid. The hydrochloride salt was then prepared by addition of dilute hydrochloric acid to an aqueous solution of the free amine. The salt was then freeze dried before being recrystallised. m.p. 149°-151° C. (methanol/diethyl ether) (lit. 148°-149° C.).

EXAMPLE 8

4,5-Anhydro-1-azido-1-deoxy-2,3-O-isopropylidene-6-O-trifluoromethanesulphonyl-D-talitol (9)

To a solution of the epoxy alcohol (6) (1.9 g, 8.6 mmol) in freshly distilled, dry dichloromethane (40 ml) at −30° C. was added dry pyridine (1.4 ml, 17.2 mmol)

followed by trifluoromethanesulphonic anhydride (2.2 ml, 13 mmol). The reaction mixture was then stirred for 15 minutes at this temperature by which time t.l.c. showed no starting material ($R_f$ 0.25) and one product ($R_f$ 0.85). The solution was then washed with dilute aqueous hydrochloric acid (10 ml), saturated copper (II) sulphate solution (10 ml) and brine (20 ml) before being dried (sodium sulphate). Removal of the solvent in vacuo then gave 4,5-anhydro-1-azido-1-deoxy-2,3-O-isopropylidene-6-O-trifluoromethanesulphonyl-D-talitol (9), as a yellow oil which was used immediately without further purification. $^1$H NMR ∂: 4.82 (1H, dd, H-6), 4.40 (2H, m, H-2, H-6'), 3.88 (1H, t, H-3), 3.55 (2H, dd, H-1, H-1'), 3.31 (1H, dt, H-5), 3.1 (1H, dd, H-4), 1.52, 1.38 (6H, 2s, CH$_3$). $^{13}$C NMR ∂: 110.0 (s, C(CH$_3$)$_2$), 76.2 (d, C-2), 75.9 (d, C-3), 75.2 (t, C-6), 53.1 (2d, C-4, C-5), 49.9 (t, C-1), 27.0, 24.5 (2q, CH$_3$).

EXAMPLE 9 tert-Butyl-8-azido-4,5-anhydro-6,7-O-isopropylidene-2,3,8-trideoxy-L-altro-octanonoate (14)

To the triflate (9) in freshly distilled, dry tetrahydrofuran (15 ml) was added, all at once, lithium tert-butyl acetate (1.6 g, 13 mmol). The reaction was then stirred for 15 minutes by which time t.l.c. (20%, ethyl acetate/hexane) showed no starting material ($R_f$ 0.4) and one product ($R_f$ 0.3). Preadsorption and flash chromatography (0–25%, ethyl acetate/hexane) then gave tert-butyl-8-azido-4,5-anhydro-6,7-O-isopropylidene-2,3,8-trideoxy-L-altro-octanonoate (14), as a colourless oil (1.7 g, 60% over three steps). $[α]_D^{20}$ +63.5° (c, 0.95 in CHCl$_3$). $ν_{max}$: 2150, 1760 cm$^{-1}$. $^1$H NMR ∂: 4.37 (1H, dt, H-7), 3.75 (1H, dd, H-6), 3.55 (2H, t, H-8, H-8'), 2.95 (1H, ddd, H-4), 2.84 (1H, dd, H-5), 2.37 (2H, t, H-3, H-3'), 2.03 (1H, m, H-2), 1.77 (1H, p, H-2'), 1.53 (3H, s, CH$_3$), 1.45 (9H, s, $^t$Bu), 1.36 (3H, s, CH$_3$). $^{13}$C NMR ∂: 172.0 (s, CO), 110.0 (s, C(CH$_3$)$_2$), 80.6 (s, C(CH$_3$)$_3$), 77.1, 76.6 (2d, C-6, C-7), 57.1 (d, C-5), 55.0 (d, C-4), 50.4 (t, C-8), 31.3 (t, C-2), 27.9 (s, CH$_3$)$_3$), 27.3, 24.8 (2q, CH$_3$), 26.5 (t, C-3). m/z (DCI, NH$_3$): 345 (M+NH$_4^+$, 15%), 328 (M+H$^+$, 5%), 300 (M+H—N$_2^+$, 20%), 244 (M+NH$_4$—CO$_2$$^t$Bu$^+$, 100%). (Found C, 54.98; H, 7.67; N, 12.56%. C$_{15}$H$_{25}$N$_3$O$_5$ requires C, 55.0; H, 7.65; N, 12.84%).

EXAMPLE 10 tert-Butyl-5,8-imino-6,7-O-isopropylidene-2,3,5,8-tetradeoxy-D-manno-octanonoate (16)

The azidoepoxide (14) (800 mg, 2.4 mmol) was stirred in ethanol (20 ml) under hydrogen with 10% palladium on carbon (60 mg) for 16 hours. The catalyst was then filtered off and the solvent removed in vacuo. Purification by flash chromatography (0–2%, methanol/chloroform) then afforded tert-butyl-5,8-imino-6,7-O-isopropylidene-2,3,5,8-tetradeoxy-D-manno-octanonoate (16), as a colourless oil (575 mg, 80%). $[α]_D^{20}$ −23.8° (c, 0.13 in CHCl$_3$). $ν_{max}$: 3400 (broad), 1719 cm$^{-1}$. $^1$H NMR ∂: 4.73 (2H, m, H-6, H-7), 3.87 (1H, s, NH), 3.16 (1H, d, H-4), 2.9 (1H, broad d, OH), 2.86–2.35 (5H, m, H-2, H-2', H-5, H-8, H-8'), 1.94 (2H, m, H-3, H-3'), 1.47 (3H, s, CH$_3$), 1.45 (9H, s, (CH$_3$)$_3$), 1.31 (3H, s, CH$_3$). $^{13}$C NMR ∂: 173.0 (s, CO), 110.9 (s, C(CH$_3$)$_2$), 82.1 (2d, C-6, C-7), 80.2 (s, C(CH$_3$)$_3$), 70.6 (d, C-4), 66.5 (d, C-5), 52.3 (t, C-8), 32.0 (t, C-2), 30.4 (t, C-3), 27.8 (q, (CH$_3$)$_3$), 25.4, 23.3 (2q, CH$_3$). m/z (CI, NH$_3$): 302 (M+H$^+$, 80%), 228 (M—O$^t$Bu$^+$, 100%).

EXAMPLE 11

(1S,2R,8R,8aR)-1,2-O-Isopropylidene-1,2,8-trihydroxyindolizidin-5-one (17)

The aminoester (16) (0.82 g, 2.7 mmol) was stirred in freshly distilled, dry methanol (25 ml) under reflux with sodium methoxide (10 mg) for 18 hours. The solvent was then removed in vacuo and the residue examined by infrared spectroscopy which showed no ester band (1719 cm$^{-1}$) and a strong lactam band (1640 cm$^{-1}$). Filtration through celite with ethyl acetate then afforded (1S,2R,8R,8aR)-1,2-O-isopropylidene-1,2,8-trihydroxyindolizidin-5-one (17), as a pale yellow solid which was recrystallised to give a white solid (570 mg, 92%). m.p. 126°–128° C. (diethyl ether) (lit: −125°–127° C.). $[α]_D^{20}$ +10.2° (c, 0.39 in methanol). $ν_{max}$ (CHCl$_3$): 3400 (broad), 1640 cm$^{-1}$. $^1$H NMR ∂: 4.80–4.70 (2H, m, H-1, H-2), 4.20 (1H, d, H-8), 4.14 (1H, m, H-8a), 3.33 (1H, dd, H-3), 3.14 (1H, dd, H-3'), 2.60–2.40 (2H, m, H-6, H-6'), 2.15 (1H, m, H-7), 1.89 (1H, m, H-7'), 1.42, 1.32 (6H, 2s, CH$_3$). $^{13}$C NMR ∂: 169.0 (s, CO), 111.9 (s, C(CH$_3$)$_2$), 79.6 (d, C-2), 77.4 (d, C-1), 66.2 (d, C-8), 64.0 (d, C-8a), 50.5 (t, C-3), 29.4 (t, C-7), 26.1, 24.4 (2q, CH$_3$). m/z (CI, NH$_3$): 228 (M+H$^+$, 50%). (Found C, 58.25; H, 7.79; N, 6.09%. C$_{11}$H$_{17}$NO$_4$ requires C, 58.15; H, 7.48; N, 6.17%).

EXAMPLE 12

(1S,2R,8R,8aR)-1,2-O-Isopropylidene-1,2,8-trihydroxyindolizidine borane (18)

To the lactam (17) (570 mg, 2.5 mmol) in freshly distilled, dry tetrahydrofuran (15 ml) was added, all at once borane:dimethyl sulphide complex (1.3 ml, 7.5 mmol). The reaction was then stirred at room temperature for 18 hours. Methanol was then added cautiously and the reaction mixture preadsorbed onto silica gel and purification by flash chromatography (0–40%, ethyl acetate/hexane) to give (1S,2R,8R,8aR)-1,2-O-Isopropylidene-1,2,8-trihydroxyindolizidine borane (18), as a colourless oil (400 mg, 70%). $ν_{max}$: 3500 (broad) cm$^{-1}$. $^1$H NMR ∂: 5.27 (1H, t, H-1), 5.06 (1H, dt, H-2), 3.85 (1H, dq, H-8), 3.44 (1H, d, H-8a), 3.32 (1H, dd, H-3), 3.23 (1H, dd, H-3'), 3.17 (1H, m, H-5), 3.04 (1H, m, H-5'), 2.10 (1H, m, H-7), 1.92 (1H, m, H-7'), 1.74 (1H, m, H-6), 1.57 (1H, m, H-6'), 1.56, 1.39 (6H, 2s, CH$_3$). $^{13}$C NMR ∂: 114.6 (s, C(CH$_3$)$_2$), 81.2 (d, C-1), 78.5 (d, C-2), 71.0 (d, C-8), 65.1 (d, C-8a), 61.6 (t, C-3), 56.3 (t, C-5), 29.0 (t, C-7), 25.3, 23.5 (2q, CH$_3$), 18.1 (t, C-6). m/z (CI, NH$_3$): 228 (M+H$^+$, 40%), 214 (M+H—BH$_3^+$, 100%).

EXAMPLE 13

Swainsonine
[(1S,2R,8R,8aR)-1,2,8-Trihydroxyindolizidine](1)

The aminoborane complex (18) (250 mg, 1.1 mmol) was stirred in trifluoracetic acid:water (1:1, 6 ml) for 48 hours. Removal of the solvent in vacuo and purification by ion exchange chromatography then gave swainsonine (1) as a white crystalline solid (160 mg, 86%). m.p. 141°–143° C. (lit. 141°–143° C.). $[α]_D^{20}$ −80.3° (c, 0.58 in methanol), (lit. −78° to −88°). $ν_{max}$ (KBr): 3500 cm$^{-1}$. $^1$H NMR (D$_2$O) ∂: 4.14 (1H, m, H-2), 4.05 (1H, dd, H-1), 3.60 (1H, ddd, H-8), 2.74 (2H, m, H-3, H-5), 2.35 (1H, dd, H-3'), 1.89–0.96 (6H, m, 5'-H, H-6, H-6', H-7, H-7', H-8a). $^{13}$C NMR ∂: 73.1, 69.7, 69.3, (3d, C-1, C-2, C-8), 66.6 (d, C-8a), 60.8, 51.9 (2t, C-3, C-5), 32.6 (t, C-7), 23.3 (t, C-6). m/z (DCI, NH$_3$): 174 (M+H$^+$, 100%), 156

(M+H—H$_2$O+, 15%). This material was identical to an authentic sample of swainsonine.

EXAMPLE 14

3,4-Anhydro-2,7-dideoxy-5,6-O-isopropylidene-L-altro-heptononitrile (15)

To the epoxytriflate (9), prepared from the diol mesylate (12) (1 g, 3.0 mmol), in freshly distilled, dry tetrahydrofuran (15 ml) chilled to 0° C. was added all at once, lithium cyanide (150 mg, 4.5 mmol). The reaction was then stirred for 1 hour at this temperature by which time t.l.c. (20%, ethyl acetate/hexane) showed no starting material (R$_f$ 0.4) and one product (R$_f$ 0.35). Addition of silica gel, removal of the solvent in vacuo and purification by flash chromatography (0–20%, ethyl acetate/hexane) then gave 3,4-anhydro-2,7-dideoxy-5,6-O-isopropylidene-L-altro-heptononitrile (15), as a colourless oil (560 mg, 77% over 3 steps). $v_{max}$ (CHCl$_3$): 3500, 2256, 2100. $^1$H NMR ∂: 4.42 (1H, dt, H-6), 3.86 (1H, t, H-5), 3.57 (2H, ABX, H-7, H-7'), 3.22 (1H, m, H-3), 3.10 (1H, dd, H-4), 2.82 (2H, ABX, H-2, H-2'), 1.54, 1.38 (6H, 2s, CH$_3$). $^{13}$C NMR ∂: 118.76 (s, CN), 110.0 (s, C(CH$_3$)$_2$), 76.2 (d, C-6), 76.0 (d, C-5), 54.8 (d, C-3), 51.5 (d, C-4), 50.2 (t, C-7), 27.2, 24.7 (2q, CH$_3$), 20.3 (t, C-2). m/z (CI, NH$_3$): 256 (M+NH$_4$+, 45%), 239 (M+H+, 15%), 211 (M+H—28+, 100%).

EXAMPLE 15

4,7-Imino-5,6-O-isopropylidene-2,4,7-trideoxy-D-manno-heptononitrile (19)

The azidocyanoepoxide (15) (560 mg, 2.4 mmol) was taken up in ethanol (15 ml) and stirred under hydrogen in the presence of 10% palladium on carbon (70 mg) for 12 hours. Filtration, removal of the solvent in vacuo and purification by flash chromatography (0–5%, methanol/chloroform) then gave one major product as a solid (360 mg, 73%) which was recrystallised to give 4,7-imino-5,6-O-isopropylidene-2,4,7-trideoxy-D-manno-heptononitrile (19), as a white crystalline solid. m.p. 91°–92° C. (ethyl acetate/hexane). $[\alpha]_D^{20}$ —77.2° (c, 0.32 in CHCl$_3$). $v_{max}$ (KBr): 3400 (broad), 2250 cm$^{-1}$. $^1$H NMR ∂: 4.76 (2H, m, H-5, H-6), 4.23 (1H, q, H-3), 3.18 (1H, d, H-4), 2.79 (3H, H-2, H-7, H-7'), 2.68 (1H, q, H-2'), 1.48, 1.33 (6H, 2s, CH$_3$). $^{13}$H NMR ∂: 118.04 (s, CN), 111.28 (s, C(CH$_3$)$_2$), 81.99, 81.84 (2d, C-5, C-6), 66.72 (d, C-3), 66.28 (d, C-4), 52.58 (t, C-7), 24.54 (q, CH$_3$), 24.41 (t, C-2), 23.51 (q, CH$_3$). m/z (CI, NH$_3$): 213 (M+H+, 100%), 195 (M+H—18+, 40%), 142 (M—CHOHCH$_2$CN+, 25%). (Found C, 57.20; H 7.26; N 13.05%. C$_{10}$H$_{16}$N$_2$O$_3$ requires C, 56.9; H, 7.54; N, 13.27%).

EXAMPLE 16

N-Benzyloxycarbonyl-4,7-imino-5,6-O-isopropylidene-2,4,7-trideoxy-D-manno-heptononitrile (20)

To the amine (19) (1.4 g, 6.6 mmol) in a vigorously stirred mixture of ethyl acetate:saturated sodium hydrogen carbonate solution (3:2, 25 ml) was added benzyl chloroformate (1.6 ml, 10 mmol). After 3 hours t.l.c. (50%, ethyl acetate/hexane) showed no starting material (R$_f$ 0.0), benzyl alcohol (R$_f$ 0.7) and one product (R$_f$ 0.6). Separation of the organic layer and extraction of the aqueous layer with ethyl acetate (2×15 ml) followed by washing of the combined organics with brine (40 ml) and drying (sodium sulphate) gave, after evaporation, the crude product which was preadsorbed and purified by flash chromatography (0–50%, ethyl acetate/hexane) to give N-benzyloxycarbonyl-4,7-imino-5,6-O-isopropylidene-2,4,7-trideoxy-D-manno-heptononitrile (20), as a white solid (2 g, 88%). m.p. 100°–101° C. (ethyl acetate/hexane). $[\alpha]_D^{20}$ —29.3° (c 0.47 in CHCl$_3$). $v_{max}$: 3350, 2251, 1672 cm$^{-1}$. $^1$H NMR ∂: 7.40 (5H, m, ArH), 5.15 (2H, q, PhCH$_2$), 4.87 (1H, t, H-5), 4.77 (1H, q, H-6), 4.24 (1H, s, H-3), 4.10 (1H, dd, H-7), 3.9 (1H, s, H-4), 3.50 (1H, m, H-7'), 2.73 (1H, dd, H-2), 2.52 (1H, dd, H-2'), 1.55, 1.36 (6H, 2s, CH$_3$). $^{13}$C NMR ∂: 136.0, 128.0 (Ar), 113.7 (s, C(CH$_3$)$_2$), 80.12, 79.9, 77.8, 77.6, (4d, C-3, C-4, C-5, C-6), 68.0, 67.7 (2d, C-7, PhCH$_2$), 26.1, 24.2 (2q, CH$_3$), 23.0 (t, C-2). m/z (DCI, NH$_3$): 364 (M+NH$_4$+, 25%), 347 (M+H+, 95%), 303 (M—H$_2$O—CN+, 100), 213 (M+2H—CO$_2$CH$_2$Ph+, 55%), 91 (CH$_2$Ph+, 90%). (Found C, 62.55; H, 6.50; N, 8.26%. C$_{18}$H$_{22}$N$_2$O$_5$ requires C, 62.4; H, 6.36; N, 8.09%).

EXAMPLE 17

N-Benzyloxycarbonyl-4,7-imino-5,6-O-isopropylidene-2,4,7-trideoxy-D-manno-heptonamide (21)

The cyanide (20) (1.2 g, 3.5 mmol) was stirred for 3 days in methanol (20 ml) with sodium carbonate (220 mg, 2.6 mmol), hexene (4.1 ml, 31.5 mmol) and 30% hydrogen peroxide (3.8 ml, 33.4 mmol). Saturated sodium metabisulphite solution was then added slowly and the reaction mixture extracted with ethyl acetate (3×30 ml). The combined organic extracts were then washed with brine (70 ml) before being dried (sodium sulphate). Removal of the solvent in vacuo followed by purification by flash chromatography (0–100%, ethyl acetate/hexane) then gave N-benzyloxycarbonyl-4,7-imino-5,6-O-isopropylidene-2,4,7-trideoxy-D-manno-heptonamide (21), as a white solid (1.2 g, 94%). m.p. 102°–103° C. (ethyl acetate/hexane). v —18.5° (c, 0.66 in CHCl$_3$). $v_{max}$: 3400 broad, 1710–1780 cm$^{-1}$. $^1$H NMR ∂: 7.40 (5H, m, ArH), 5.3 (1H, Bs, NH), 5.12 (2H, q, CH$_2$), 4.87 (1H, t, H-5), 4.75 (1H, m, H-6), 4.36 (1H, m, H-3), 4.12 (1H, t, H-4), 4.00 (1H, s, H-7), 3.40 (1H, m, H-7'), 2.50–2.30 (2H, m, H-2, H-2'), 1.57, 1.35 (6H, 2s, CH$_3$). $^{13}$C NMR ∂ 174.0 (s, CO), 136.0, 128.0 (Ar), 113.7 (s, C(CH$_3$)$_2$), 80.0, 77.7 (3d, C-3, C-5, C-6), 67.9 (d, C-4), 67.6 (t, PhCH$_2$), 51.0 (t, C-7), 40.0 (t, C-2), 26.1, 24.4 (2q, CH$_3$). m/z (DCI NH$_3$): 365 (M+H+, 100%), 91 (PhCH$_2$+, 80%). (Found C, 59.49; H, 6.90; N, 7.81%. C$_{18}$H$_{24}$N$_2$O$_6$ requires C, 59.34; H, 6.59; N, 7.69%).

EXAMPLE 18

N-Benzyloxycarbonyl-3-O-tert-butyldimethylsilyl-4,7-imino-5,6-O-isopropylidene-2,4,7-trideoxy-D-manno-heptonamide (22)

To the alcohol (21) (374 mg, 1.02 mmol) in dry, freshly distilled, dichloromethane (15 ml) was added dry pyridine (0.55 ml, 6.12 mmol) and tert-butyldimethylsilyl trifluoromethanesulfonate (0.94 ml, 4.08 mmol). The reaction was then stirred for 3 hours at room temperature by which time t.l.c. (50%, ethyl acetate/hexane) showed no starting material (R$_f$ 0.0) and one product (R$_f$ 0.3). The solution was then washed with dilute aqueous hydrochloric acid (10 ml) then brine (10 ml) and dried (sodium sulphate). Removal of the solvent in vacuo and purification of the residue by flash chromatography (0–90%, ethyl acetate/hexane) then gave N-benzyloxycarbonyl-3-O-tert-butyldimethylsilyl-4,7-imino-5,6-O-isopropylidene-2,4,7-trideoxy-D-manno-heptonamide (22), as a white solid (480 mg, 98%). m.p. 121°–122° C. (hexane/ethyl acetate). $[\alpha]_D^{20}$ —28.8° (c, 0.53 in CHCl$_3$). $v_{max}$(KBr): 3447, 3356, 1684 cm$^{-1}$. $^1$H NMR ∂: 7.40 (5H, m, ArH), 5.70 (1H, s, NH), 5.11 (3H, PhCH$_2$, NH), 4.79 (1H, t, H-5), 4.70 (1H, q, H-6), 4.59 (1H, q, H-3), 4.16 (1H, t, H-4), 4.01 (1H, dd, H-7), 3.16 (1H, dd, H-7'), 2.61 (1H, dd, H-2), 2.39 (1H, dd, H-2'), 1.54, 1.33 (6H, 2s, CH$_3$), 0.88 (9H, s, C(CH$_3$)$_3$), 0.09 (6H, s, CH$_3$). $^{13}$C NMR ∂: 173 (s, CO), 136.0 (Ar), 128.0 (s, Ar), 113.0 (s, C(CH$_3$)$_2$), 79.6, 77.9 (2d, C-5, C-6), 68.0 (d, C-3), 67.1 (t, PhCH$_2$), 63.5 (d, C-4), 50.9 (t, C-7), 40.9 (t, C-2), 27.0 (q, CH$_3$), 25.7 (q, C(CH$_3$)$_3$), 25.0 (q, CH$_3$), 17.8 (s, C(CH$_3$)$_3$), −4.7, −5.1 (2q, SiCH$_3$). m/z (DCI, NH$_3$): 479 (M+H$^+$, 100%), 421 (M+H—CH$_2$CONH$_2$$^+$, 25%), 345 (M+2H—CO$_2$CH$_2$Ph$^+$, 80%), 328 (M+2H—CO$_2$CH$_2$Ph—NH$_3$$^+$, 50%), 91 (CH$_2$Ph$^+$, 70%). (Found C, 60.50; H, 8.37; N, 6.19%. C$_{24}$H$_{38}$N$_2$O$_6$Si requires C, 60.30; H, 7.95; N, 5.86%).

EXAMPLE 19

3-O-tert-Butyldimethylsilyl-4,7-imino-5,6-O-isopropylidene-2,4,7-trideoxy-D-manno-heptonamide (23)

The protected amine (22) (360 mg, 0.75 mmol) was stirred in ethanol (15 ml) in the presence of 10% palladium on carbon (70 mg) under hydrogen for 1 hour by which time no starting material (R$_f$ 0.75) remained by t.l.c. (70%, ethyl acetate/hexane). Filtration and removal of the solvent then gave 3-O-tert-butyldimethylsilyl-4,7-imino-5,6-O-isopropylidene-2,4,7-trideoxy-D-manno-heptonamide (23), as a white solid (235 mg, 91%). m.p. 143°–144° C. (ethyl acetate). [α]$_D^{20}$ −55.0° (c, 0.26 in CHCl$_3$). υ$_{max}$ (KBr): 3400 (broad), 1678 cm$^{-1}$. $^1$H NMR ∂: 6.5, 5.8 (2H, 2Bs, NH$_2$), 4.59 (2H, m, H-3, H-2), 4.26 (1H, dt, H-5), 3.04 (1H, d, H-1), 2.75–2.47 (4H, H-6, H-6', H-4, H-1'), 1.41, 1.25 (6H, 2s, CH$_3$), 0.86 (9H, s, C(CH$_3$)$_3$), 0.10 (6H, s, Si(CH$_3$)$_2$). $^{13}$C NMR ∂: 173.5 (s, CO), 110.3 (s, C(CH$_3$)$_2$), 81.3, 80.1 (2d, C-3, C-2), 67.8 (d, C-5), 67.4 (d, C-4), 53.0 (t, C-1), 42.2 (t, C-6), 25.6 (q, (CH$_3$)$_3$), 23.3 (q, CH$_3$), 17.8 (s, C(CH$_3$)$_3$), −4.9, −5.3 (2q, SiCH$_3$). m/z (DCI, NH$_3$): 345 (M+H$^+$, 100%), 328 (M+H—NH$_3$$^+$, 35%).

EXAMPLE 20

(1S,2R,7R,7aR)-7-O-tert-Butyldimethylsilyl-1,2-O-isopropylidene-1,2,7-trihydroxypyrrolizidin-5-one (24)

The aminoamide (23) (225 mg, 0.65 mmol) was stirred at 80° C. for 1 hour in carbon tetrachloride (8 ml) with sodium hydrogen carbonate (15 mg). T.l.c. (20%, methanol/chloroform) then showed that no starting material (R$_f$ 0.2) remained and one product (R$_f$ 0.95) had been formed. The reaction mixture was then filtered and the solvent removed in vacuo. Recrystallisation of the residue gave (1S,2R,7R,7aR)-7-O-tert-butyldimethylsilyl-1,2-O-isopropylidene-1,2,7-trihydroxypyrrolizidin-5-one (24), as a white crystalline solid (195 mg, 92%). m.p. 106°–109° C. (hexane). [α]$_D^{20}$ −27.2° (c, 0.54 in CHCl$_3$). υ$_{max}$: 1690 cm$^{-1}$. $^1$H NMR ∂: 4.79 (1H, t, H-1), 4.62 (2H, m, H-2, H-7), 3.94 (1H, d, H-3), 3.64 (1H, dd, H-7a), 2.98 (1H, ddd, H-3'), 2.77 (1H, dd, H-6), 2.54 (1H, ddd, H-6'), 1.38, 1.29 (6H, 2s, CH$_3$), 0.91 (9H, s, C(CH$_3$)$_3$), 0.11 (6H, s, SiCH$_3$). $^{13}$C NMR ∂: 174.9 (s,CO), 112.1 (s, C(CH$_3$)$_2$), 81.9, 78.3 (2d, C-1, C-2), 73.0 (d, C-7), 65.1 (d, C-7a), 48.2 (t, C-3), 44.0 (t, C-6), 26.1 (q, CH$_3$), 25.5 (q, C(CH$_3$)$_3$), 24.0 (q, CH$_3$), 17.7 (s, C(CH$_3$)$_3$), −5.05, −5.16 (2q, SiCH$_3$). m/z (DCI, NH$_3$): 328 (M+H$^+$, 100%). (Found C, 58.68; H, 9.18; N, 4.13%. C$_{16}$H$_{29}$NO$_4$Si requires C, 58.7; H, 8.87; N, 4.28%).

EXAMPLE 21

(1S,2R,7R,7aR)-7-O-tert-Butyldimethylsilyl-1,2-O-isopropylidene-1,2,7-trihydroxypyrrolizidine borane (26)

To the lactam (24) (270 mg, 0.83 mmol) in freshly distilled, dry, tetrahydrofuran (8 ml) was added a tetrahydrofuran solution of diborane/dimethylsulphide complex (0.42 ml, 4.2 mmol). The reaction was then left for 12 hours at room temperature before being quenched carefully with methanol. Preadsorption and purification by flash chromatography (0–15%, ethyl acetate/hexane) then gave (1S,2R,7R,7aR)-7-O-tert-butyldimethylsilyl-1,2-O-isopropylidene-1,2,7-trihydroxypyrrolizidine (26), as a colourless oil (170 mg, 70%). υ$_{max}$ (CHCl$_3$): 2400 cm$^{-1}$. $^1$H NMR ∂: 4.97 (1H, q, H-2), 4.84 (1H, t, H-1), 4.67 (1H, quin, H-7), 3.71 (1H, dd, H-3), 3.49 (2H, m, H-3', H-7a), 3.15 (1H, m, H-5), 2.89 (1H, dd, H-5'), 2.28–2.02 (2H, m, H-6, H-6'), 1.50, 1.33 (6H, 2s, CH$_3$), 0.90 (9H, s, C(CH$_3$)$_3$), 0.09 (6H, s, SiCH$_3$). $^{13}$C NMR ∂: 113 (s, C(CH$_3$)$_2$), 82.5, 79.9 (2d, C-1, C-2), 79.5 (d, C-7), 71.8 (d, C-7a) 64.6 (t, C-3), 61.2 (t, C-5), 34.9 (t, C-6), 27.0 (q, CH$_3$), 25.5 (q, C(CH$_3$)$_3$), 24.6 (q, CH$_3$), 17.6 (s, C(CH$_3$)$_3$), −5.03, −5.14 (2q, SiCH$_3$).

EXAMPLE 22

(1S,2R,7R,7aR)-1,2,7-Trihydroxypyrrolizidine (3)

The borane adduct (26) (170 mg, 0.52 mmol) was dissolved in trifluoroacetic acid: water (1:1, 4 ml) and stirred for 24 hours at room temperature. Removal of the solvent in vacuo and purification by ion exchange chromatography with Dowex 50(H) followed by Amberlite CG-400(Cl) resins then gave (1S,2R,7R,7aR)-1,2,7-trihydroxypyrrolizidine (3), as a gum which was recrystallised to give a white solid (57 mg, 68%). m.p. 150°–153° C. (ethanol). [α]$_D^{20}$ −29.3° (c, 0.15 in MeOH). υ$_{max}$ (KBr): 3400, 3270 cm$^{-1}$. $^1$H NMR (D$_2$O) ∂: 4.40 (1H, q, H-7), 4.04 (1H, m, H-2), 3.98 (1H, q, H-1), 3.08 (1H, t, H-7a), 2.94 (2H, m, H-3, H-5), 2.48 (1H, m, H-5'), 2.33 (1H, t, H-3'), 2.01 (1H, s, H-6), 1.62 (1H, m, H-6'). $^{13}$C NMR ∂: 73.7, 73.1 (2d, C-1, C-2), 70.9 (d, C-7), 70.6 (d, C-7a), 56.0 (t, C-3), 53.5 (t, C-5), 34.8 (t, C-6). m/z (DCI, NH$_3$): 160 (M+H$^+$, 35%). (Found C, 52.79; H, 8.33; N, 8.53%. C$_7$H$_{13}$NO$_3$ requires C, 52.83; H, 8.18; N, 8.81%).

EXAMPLE 23

(1S,2R,7R,7aR)-1,2-O-Isopropylidene-1,2,7-trihydroxypyrrolizidin-5-one (25)

To the silyl alcohol (24) (130 mg, 0.38 mmol) in freshly distilled dry tetrahydrofuran (5 ml) was added tetrabutylammonium fluoride in tetrahydrofuran (0.76 ml, 0.76 mmol). The solution was then stirred for 2 hours at room temperature. T.l.c. (10%, methanol/ethyl acetate) then showed no starting material (R$_f$ 0.9) and one product (R$_f$ 0.4). Preadsorption and purification by flash chromatography (0–10%, methanol/ethyl acetate) then gave (1S,2R,7R,7aR)-1,2-O-isopropylidene-1,2,7-trihydroxypyrrolizidin-5-one (25), as a white solid (84 mg, 100%). m.p. 148°–149° C. (ethyl acetate). [α]$_D^{20}$ 0° (c, 0.305 in CHCl$_3$). υ$_{max}$: 3360, 1669 cm$^{-1}$. $^1$H NMR ∂: 4.80 (1H, t, H-2), 4.67 (2H, m, H-1, H-7), 3.97 (1H, d, H-3), 3.70 (1H, dd, H-7a), 3.00 (1H, dd, H-3'), 2.85 (1H, dd, H-6), 2.58 (1H, ddd, H-6'), 2.50 (1H, t, OH), 1.37, 1.28 (6H, 2s, CH$_3$). $^{13}$C NMR ∂: 175.9 (s, CO), 112.1 (s, C(CH$_3$)$_2$), 81.8, 78.5 (2d, C-1, C-2), 72.7

(d, C-7), 64.4 (d, C-7a), 48.6 (t, C-3), 43.6 (t, C-6), 26.1, 23.9 (2s, $CH_3$). m/z (CI, $NH_3$): 231 ($M+NH_4^+$, 20%), 214 ($M+H^+$, 100%), 198 ($M+H-O^+$, 30%), 196 ($M+H-H_2O^+$). (Found C, 56.27; H, 6.89; N 6.35%. $C_{10}H_{15}NO_4$ requires C, 56.34; H, 7.04; N, 6.57%).

EXAMPLE 24

(1S,2R,7aS)-1,2-Dihydroxy-1,2-O-isopropylidenepyrrolizidin-5,7-dione (28)

To the alcohol (25) (77 mg, 0.36 mmol) in freshly distilled dry dichloromethane (7 ml) was added pyridinium chlorochromate (155 mg, 0.72 mmol) and 4 Å powdered molecular sieve (155 mg). The reaction was then stirred for 1 hour by which time t.l.c. (10%, methanol/ethyl acetate) showed no starting material ($R_f$ 0.4) and one product ($R_f$ 0.5). Silica gel was then added and the solvent removed in vacuo. Purification by flash chromatography (0-10%, methanol/ethyl acetate) then gave (1S,2R,7aS)-1,2-dihydroxy-1,2-O-isopropylidenepyrrolizidin-5,7-dione (28) slightly contaminated with chromate residues which was used immediately. $\upsilon_{max}$: 1775, 1698 cm$^{-1}$. $^1$H NMR ∂: 4.83 (2H, m, H-1, H-2), 4.34 (1H, d, H-3), 4.08 (2H, m, H-3′, H-7a), 3.10 (2H, m, H-6, H-6′), 1.38, 1.26 (6H, 2s, $CH_3$). $^{13}$C NMR ∂: 172.1 (s, CO), 112.7 (s, $C(CH_3)_2$), 81.5, 80.0 (2d, C-1, C-2), 72.7 (d, C-7a), 50.3 (t, C-3), 43.4 (t, C-6), 26.0, 23.6 (2q, $CH_3$).

EXAMPLE 25

(1S,2R,7S,7aR)-1,2-O-Isopropylidene-1,2,7-trihydroxypyrrolizidin-5-one (29)

To the ketone (28) in ethanol (5 ml) at 0° C. was added sodium borohydride (30 mg, 0.72 mmol). The reaction was then stirred at 0° C. for 15 minutes by which time t.l.c. (10%, methanol/ethyl acetate) showed no starting material ($R_f$ 0.5) and one product ($R_f$ 0.4). The reaction was then quenched with ammonium chloride before being preadsorbed onto silica gel and purified by flash chromatography (0-10%, methanol/ethyl acetate) to give (1S,2R,7S,7aR)-1,2-O-isopropylidene-1,2,7-trihydroxypyrrolizidin-5-one (29), as a white crystalline solid (72 mg, 94%). m.p. 132°-134° C. (ethyl acetate). $[\alpha]_D^{20}$ −19.3° (c, 0.46 in $CHCl_3$). $\upsilon_{max}$: 3410, 1671 cm$^{-1}$. $^1$H NMR ∂: 4.79 (3H, m, H-1, H-2, H-7), 4.08 (1H, d, H-3), 3.85 (1H, dd, H-7a), 3.58 (1H, d, OH), 2.94 (2H, m, H-3′, H-6), 2.40 (1H, dd, H-6′), 1.46, 1.31 (6H, 2s, $CH_3$). $^{13}$C NMR ∂: 175.6 (s, CO), 112.7 (s, $C(CH_3)_2$), 82.1, 80.2 (2d, C-1, C-2), 66.8 (d, C-7), 65.5 (d, C-7a) 49.5 (t, C-1), 42.7 (t, C-6), 26.0, 23.9 (2q, $CH_3$). m/z (CI, $NH_3$): 231 ($M+NH_4^+$, 15%), 214 ($M+H^+$, 100%). (Found C, 56.45; H, 7.16; N, 6.34%. $C_{10}H_{15}NO_4$ requires C, 56.3; H, 7.04 N, 6.57%).

EXAMPLE 26

(1S,2R,7S,7aR)-1,2-O-Isopropylidene-1,2,7-trihydroxypyrrolizidine borane (27)

To the lactam (29) (70 mg, 0.32 mmol) in freshly distilled, dry tetrahydrofuran (8 ml) was added diborane/dimethylsulphide complex solution (0.1 ml, 0.98 mmol). The reaction was then left for 12 hours at room temperature before being quenched carefully with methanol. Preadsorption and purification by flash chromatography (0-40%, ethyl acetate/hexane) then gave (1S,2R,7S,7aR)-1,2-O-isopropylidene-1,2,7-trihydroxypyrrolizidine borane (27), as a colourless oil (50 mg, 72%). $\upsilon_{max}$: 3220, 2364 cm$^{-1}$. $^1$H NMR ∂: 5.01-4.86 (3H, m, H-1, H-2, H-7), 3.67-3.28 (5H, m, H-3, H-3′, H-5, H-5′, H-7a), 2.64 (1H, m, H-6), 1.93 (1H, m, H-6′), 1.57, 1.35 (6H, 2s, $CH_3$). $^{13}$C NMR ∂: 112.1 (s, $C(CH_3)_2$), 81.7, 80.5 (2d, C-1, C-2), 75.9, 72.9 (2d, C-7, C-7a), 66.1, 59.5 (2t, C-3, C-5), 34.9 (t, C-6), 25.8, 23.1 (2q, $CH_3$).

EXAMPLE 27

(1S,2R,7S,7aR)-1,2,7-Trihydroxypyrrolizidine (4)

The borane adduct (27) (50 mg, 0.24 mmol) was dissolved in trifluoroacetic acid: water (1:1, 4 ml) and stirred for 24 hours at room temperature. Removal of the solvent in vacuo and purification by ion exchange chromatography with Dowex 50(H) followed by amberlite CG-400(Cl) then gave (1S,2R,7S,7aR)-1,2,7-trihydroxypyrrolizidine (4), as a gum (27 mg, 70%) which crystallised on trituration with diethyl ether. m.p. 125°-127° C. $[\alpha]_D^{20}$ −6.9° (c, 0.13 in MeOH). $\upsilon_{max}$ (KBr): 3395, 3269 cm$^{-1}$. $^1$H NMR ($D_2O$) ∂: 4.38 (1H, q, H-7, $J_{1,2}$ 4.2 Hz, $J_{1,3}$ 8.5 Hz), 4.25 (1H, dd, H-1, $J_{1,2}$ 1.4 Hz, $J_{1,3}$ 5.9 Hz), 4.04 (1H, m, H-2), 3.37 (1H, t, H-7a, $J_{1,2}$ 5.6 Hz), 3.08 (1H, dd, $J_{1,2}$ 4.8 Hz, $J_{1,3}$ 10.4 Hz), 3.00 (1H, m, H-5), 2.72 (1H, m, H-5′), 2.61 (1H, dd, H-1′, $J_{1,2}$ 2.9 Hz, $J_{1,3}$ 10.6 Hz), 1.75 (2H, m, H-6, H-6′). $^{13}$C NMR ∂: 73.1 (d, C-1, C-2), 72.8 (d, C-7), 68.0 (d, C-7a), 57.3 (t, C-3), 53.5 (t, C-5), 35.6 (t, C-6). m/z (DCI, $NH_3$): 160 ($M+H^+$, 40%). (Found C, 52.56; H, 8.69; N, 8.76%. $C_7H_{13}NO_3$ requires C, 52.83; H, 8.18; N, 8.81%).

Various other examples will be apparent to the person skilled in the art after reading the present disclosure without departing from the spirit and scope of the invention. It is intended that all such other examples be included within the scope of the appended claims.

What is claimed is:

1. (1S,2R,7R,7aR)-1,2,7-Trihydroxypyrrolizidine.
2. A method for the synthesis of (1S,2R,7R,7aR)-1,2,7-trihydroxypyrrolizidine comprising:
   (a) reacting 4,5-anhydro-1-azido-1-deoxy-2,3-O-isopropylidene-6-O-trifluoromethanesulphonyl-D-talitol with lithium cyanide to form an azidocyanoepoxide,
   (b) catalytically hydrogenating the azido-cyanoepoxide to give an amine,
   (c) protecting the nitrogen on the amine by reaction of said amine with benzyloxychloroformate to give a benzyloxycarbonyl derivative,
   (d) partially hydrolyzing the benzyloxycarbonyl derivative by hydrogen peroxide to give an amide,
   (e) silylating the amide to give a protected amide,
   (f) removing the benzyloxycarbonyl protecting group by acid hydrolysis to give an aminoamide,
   (g) treating the aminoamide with sodium hydrogen carbonate to give a lactam,
   (h) treating the lactam with borane:dimethyl sulfide complex to afford an amine borane adduct and
   (i) removing the isopropylidine and silyl protecting groups and the borane group in the amine borane adduct by acid hydrolysis to give (1S,2R,7R,7aR)-1,2,7-trihydroxypyrrolizidine.
3. (1S,2R,7S,7aR)-1,2,7-Trihydroxypyrrolizidine.
4. A method for the syntheses of (1S,2R,7S,7aR)-1,2,7-trihydroxypyrrolizidine comprising:
   (a) reacting (1S,2R,7R,7aR)-7-O-tert-butyldimethylsilyl-1,2-O-isopropylidene-1,2,7-trihydroxypyrrolizidin-5-one with fluoride ion to remove the silyl protecting group and give an alcohol,
   (b) oxidizing the alcohol to give the corresponding ketone, (c) reducing the ketone with sodium borohydride to give the inverted lactam,
(d) reducing the lactam with borane:dimethyl sulfide complex to afford a borane adduct and
(e) removing the isopropylidine protecting group and the borane group in the borane adduct by acid hydrolysis to give (1S,2R,7S,7aR)-1,2,7-trihydroxypyrrolizidine.

* * * * *